(12) United States Patent
Brodbeck et al.

(10) Patent No.: US 9,746,194 B2
(45) Date of Patent: Aug. 29, 2017

(54) THIN FILM CAPILLARY VAPORIZATION: DEVICE AND METHODS

(75) Inventors: Kelly J. Brodbeck, Danville, CA (US); Warren S. Breslau, Berkeley, CA (US); Erick M. Davidson, Piedmont, CA (US)

(73) Assignee: Vapore, LLC, Concord, CA (US)

( * ) Notice: Subject to any disclaimer, the term of this patent is extended or adjusted under 35 U.S.C. 154(b) by 1698 days.

(21) Appl. No.: 13/007,641

(22) Filed: Jan. 16, 2011

(65) Prior Publication Data

US 2011/0210458 A1 Sep. 1, 2011

Related U.S. Application Data

(63) Continuation-in-part of application No. 11/920,320, filed on Nov. 13, 2007, now Pat. No. 7,920,777,
(Continued)

(51) Int. Cl.
| | |
|---|---|
| *A01G 13/06* | (2006.01) |
| *F24F 6/08* | (2006.01) |
| *A61M 16/10* | (2006.01) |
| *A61M 16/16* | (2006.01) |
| *B01B 1/08* | (2006.01) |
| *B01D 5/00* | (2006.01) |

(Continued)

(52) U.S. Cl.
CPC ............ *F24F 6/08* (2013.01); *A61M 16/0833* (2014.02); *A61M 16/109* (2014.02); *A61M 16/1075* (2013.01); *A61M 16/142* (2014.02); *A61M 16/147* (2014.02); *A61M 16/16* (2013.01); *B01B 1/08* (2013.01); *B01D 5/006* (2013.01); *A61M 2205/3368* (2013.01); *A61M 2205/3653* (2013.01)

(58) Field of Classification Search
None
See application file for complete search history.

(56) References Cited

U.S. PATENT DOCUMENTS

| | | | |
|---|---|---|---|
| 3,262,290 A | 7/1966 | Huber | |
| 3,542,245 A | 11/1970 | Racek | |

(Continued)

FOREIGN PATENT DOCUMENTS

| | | |
|---|---|---|
| JP | 63-134848 A1 | 6/1988 |
| JP | 11-505318 A1 | 5/1995 |

(Continued)

*Primary Examiner* — Thor Campbell
(74) *Attorney, Agent, or Firm* — The Firenza Group Ltd.; Sharon R. Kantor

(57) ABSTRACT

The present invention relates to an apparatus and method for the generation of directed vapor from a liquid source. Vaporization takes place within a device capable of confining boiling to a geometrically small volume, and expelling it as heated vapor via capillary vaporization. The foregoing is accomplished through the use of a lightweight, compact and portable personal vaporization device that generates heated vapor by the flash boiling of small volumes of aqueous liquid in a safe and energy-efficient manner. Further, the production of vapor absent microbes in aqueous systems is accomplished through the combination of microporous componentry and flash vaporization. The apparatus and methods are directed toward personal humidification for comfort and therapeutic purposes in the case of aqueous liquids, but may also be used with other, non-aqueous liquids.

20 Claims, 4 Drawing Sheets

Figure 1:
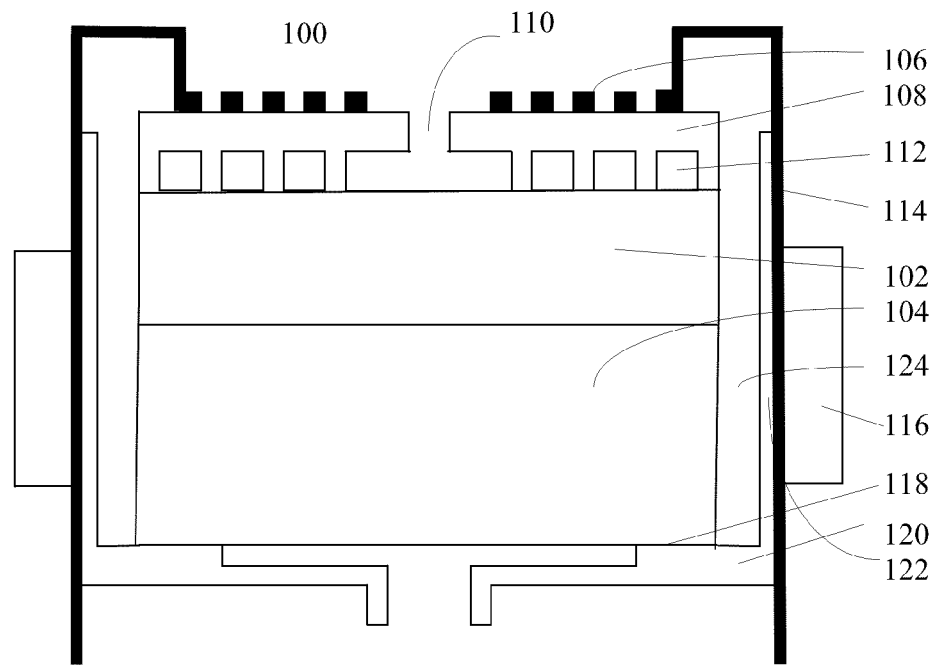

Related U.S. Application Data which is a continuation-in-part of application No. 12/095,481, filed on Jun. 16, 2009, now abandoned.

(51) Int. Cl.
*A61M 16/08* (2006.01)
*A61M 16/14* (2006.01)

(56) References Cited

U.S. PATENT DOCUMENTS

| | | |
|---|---|---|
| 3,820,540 A | 6/1974 | Hirtz et al. |
| 3,869,242 A | 3/1975 | Schladitz |
| 4,207,055 A | 6/1980 | Tanaka |
| 4,325,345 A | 4/1982 | Wilkinson et al. |
| 4,365,952 A | 12/1982 | Ohmukai et al. |
| 4,532,088 A | 7/1985 | Miller |
| 4,552,124 A | 11/1985 | Nakajima |
| 4,571,481 A | 2/1986 | Leary |
| 4,635,630 A | 1/1987 | Noir et al. |
| 4,684,341 A | 8/1987 | Kawamura et al. |
| 4,849,604 A | 7/1989 | Woolcott |
| 4,857,421 A | 8/1989 | Ernst |
| 4,937,053 A | 6/1990 | Harvey |
| 5,039,351 A | 8/1991 | Cooper et al. |
| 5,113,478 A | 5/1992 | Nakashima et al. |
| 5,228,922 A | 7/1993 | Sievers |
| 5,692,095 A | 11/1997 | Young |
| 5,870,525 A | 2/1999 | Young |
| 5,928,436 A | 7/1999 | Borkowski et al. |
| 5,929,371 A | 7/1999 | Svedberg et al. |
| 5,938,693 A | 8/1999 | Carminucci |
| 5,939,666 A | 8/1999 | Sievers et al. |
| 5,940,577 A | 8/1999 | Steinel |
| 5,998,728 A | 12/1999 | Sievers et al. |
| 6,162,046 A | 12/2000 | Young et al. |
| 6,169,852 B1 | 1/2001 | Liao et al. |
| 6,347,936 B1 | 2/2002 | Young et al. |
| 6,585,509 B2 | 7/2003 | Young et al. |
| 6,634,864 B1 | 10/2003 | Young et al. |
| 6,755,398 B1 | 6/2004 | Wong |
| 7,329,837 B2 | 2/2008 | Willkens |
| 7,431,570 B2 | 10/2008 | Young et al. |
| 7,920,777 B2 | 4/2011 | Rabin et al. |
| 7,942,644 B2 | 5/2011 | Young et al. |
| 8,201,752 B2 | 6/2012 | Brodbeck et al. |
| 2004/0151598 A1 | 8/2004 | Young et al. |
| 2006/0196968 A1 | 9/2006 | Rabin et al. |
| 2009/0220222 A1 | 9/2009 | Rabin et al. |
| 2010/0142934 A1 | 6/2010 | Sellers et al. |
| 2011/0210458 A1 | 9/2011 | Brodbeck et al. |

FOREIGN PATENT DOCUMENTS

| | | |
|---|---|---|
| WO | WO 2006124757 A2 | 11/2006 |
| WO | WO 2007064909 A2 | 6/2007 |

THIN FILM CAPILLARY VAPORIZATION: DEVICE AND METHODS

The present invention is a continuation-in-part of commonly-assigned and co-pending applications for U.S. patent Ser. No. 11/920,320 to Rabin, et al., filed 13 Nov. 2007, and U.S. Ser. No. 12/095,481 to Sellers, et al., filed 16 Jun. 2009.

BACKGROUND OF THE INVENTION

1. Field of the Invention

The present invention relates to an apparatus and method for the generation and safe delivery of disinfected, therapeutic vapor. More specifically, the present invention provides a vaporizer device and vaporization method for the flash boiling of small volumes of aqueous liquid to heated vapor in a safe and energy-efficient manner using a lightweight, compact and portable personal vaporization device.

2. Discussion of the Related Art

One class of devices that can be used to generated vapor from liquid at room temperature is known in the art as capillary pumps, capillary vaporization modules or capillary force vaporizers. These devices generate pressurized vapor directly from unpressurized liquid by applying heat to cause liquid to boil within a capillary member, and by at least partially constraining the evolved vapor to allow pressure to increase, and then exit the device through one or more orifices as a high velocity jet. Such devices are thermally powered, compact, and generally have no moving parts, thereby offering certain advantages over other techniques used for liquid vaporization and vapor pressurization. Capillary force vaporizers and devices in which they may be found are variously described in U.S. Pat. Nos. 5,692,095; 5,870,525; 6,162,046; 6,347,936; 6,585,509 and 6,634,864.

For decades, the vaporization of liquids for humidification purposes has been recommended by physicians for a wide range of medical conditions. Consumers have also found humidification useful and beneficial for various aspects of personal care. Physicians regard humidification as part of "supportive care," that is, any intervention that helps to relieve symptoms and provide comfort to a patient in addition to rest, fever control, and hydration. Consumers have used humidification for purposes such as skin moisturization and as an aid in cleansing.

As the popularity of humidification sources in the form of room humidifiers rose towards the latter part of the 20$^{th}$ century, however, humidifier-related problems surfaced. According to medical literature, for example, the use of room humidifiers can lead to an increase in the presence of allergens related to mold and dust mites, as humidifiers can promote the growth of such organisms in a room. Moreover, thermal injuries have been associated with the use of warm mist room humidifiers when abundant volumes of hot or boiling water are inadvertently spilled on a patient during humidifier use or during the time required to heat water. Cool mist room humidifiers, on the other hand, are prone to bacterial growth in their water reservoirs and can propagate microbes during dispersion. This has lead to reports of various flu-like symptoms in some patients, which have been collectively termed "humidifier fever." Examples of cool mist humidifiers include: ultrasonic humidifiers, which produce a cool mist using ultrasonic vibrations; impeller humidifiers, which produce a cool mist with a rotating disk; and evaporators, which variously use a fan to blow air through a wet wick, filter or belt.

In addition to the foregoing problems, most prior art humidifiers require some passage of time for their liquid reservoirs to be heated to a high enough temperature to be able to provide desired vapor. Even those vaporizers that employ a liquid supply in lieu of a reservoir are not able to generate vapor instantaneously. Moreover, most prior art vaporizers do not protect against hazards due to inadvertent scalding. U.S. Pat. Nos. 4,532,088 and 4,657,713 both to Miller, K. G., for instance, teach a humidifier assembly comprising a housing, a horizontally disposed heater, a liquid water supply means, a humidification chamber with an inlet for a breathable gas and an outlet for humidified breathable gas, and a hydrophobic filter. Neither of these patents teaches a method of providing nearly instantaneous water vapor or the avoidance of scalding hazards.

U.S. Pub. No. 20090145847A1 to Spiegelman, et al., teaches methods and systems for the purification of steam that can be operated at either relatively high or relatively low operating temperatures and under sub-atmospheric pressures. However, neither the generation of nearly instantaneous, directed water vapor nor the denaturing or killing of microbes, or avoidance of scalding hazards are addressed. U.S. Pat. No. 6,367,472 to Koch describes a respiration humidifier comprising an outer jacket, a plurality of semi-permeable hydrophobic hollow fibers, a water feed, a breathing feed line and a breathing gas drain line in flow connection with an interior of the hollow fibers, and an electrical heating means for electrically heating the hollow fibers. In order to deliver the necessary heat of evaporation, however, this unit requires 60 W of power, which is equivalent to 3.6 kJ/min or more than 100 kJ over the course of 30 minutes. U.S. Pat. Nos. 6,102,037 and 6,718,973, also to Koch, describe a metering device, and an evaporation chamber for mixing, respectively, but do not describe a heating means, and thus the means for generating water vapor water.

EP2072471 to Nomura, et al., teaches a sterilization method for water that involves applying a high voltage pulse to a pair of discharge electrodes comprising a high voltage electrode and a ground electrode in the water, so that dielectric breakdown occurs and bubbles are generated in the water to cause a jet. This patent does not teach nearly instantaneous delivery of directed or pressured heated water vapor, nor the denaturing or killing of microbes. U.S. Pat. No. 3,695,267 to Hirtz, et al., teaches a tubular device for personal use, however, the tubular portion of the device must be water cooled in order to avoid potential scalding to the user. Miller, in U.S. Pat. No. 4,532,088, teaches a vented humidification space for receiving vapor passed through a hydrophobic filter mounted on a heater through which water flows. The heater requires a ball valve, however, to prevent the delivery of water to the heater if the filter is not in place.

In light of the foregoing, it would be advantageous to provide a technique for vaporization that is free from scalding hazards and that additionally does not support the transmission of microbes, bacteria or molds. In addition, it is desirable to provide a device that can provide therapeutic warmth without requiring the heating of large quantities of water. It would be also desirable to permit the generation of water or aqueous vapor in as short a time as possible, especially if that could be accomplished in an energy-efficient manner.

SUMMARY OF THE INVENTION

In light of the foregoing discussion, it is desirable to provide humidification that not only is free from scalding hazards and does not generally support the transmission of microbes, and bacteria and molds, in particular. Furthermore, it is desirable to provide a device that can provide humidification without requiring the heating of large quantities of water while permitting the generation of water vapor in as short a time as possible. In particular, it is desirable to deliver therapeutic or beneficial heat to an individual in a manner that is safe, efficient and can be accomplished quickly. Accordingly, the present invention provides an apparatus and method for the safe, nearly instantaneous generation of pressurized, germ-free water vapor from non-pressurized liquid feed.

Essentially, the inventive technique and device described herein involve the flash boiling of small volumes of aqueous liquid to yield heated vapor in a safe and energy-efficient manner using a lightweight, compact and portable personal vaporization device. An important aspect of the inventive vaporizers described herein is the minimal volume of aqueous feed that is vaporized. Conceptually, the amount of liquid that is vaporized at any time may be regarded as a thin film. As only very small amounts of liquid are heated to vaporization, the inventive vaporizers avoid many of the problems associated with prior art vaporizers, which typically involve the heating of large volumes of water to the boiling point. The vaporizers of the present invention therefore virtually obviate any potential hazards associated with scalding due to small amount of water that is being heated. At the same time, very little energy is required to generate vapor due to the small volume of water that requires heat in order to be vaporized. Rather than heating large volumes of water to boiling, the present invention uses energy for the flash boiling or the flash vaporization of a very small volume of water. A third feature of vaporizers of the present invention is that the generation of vapor is nearly instantaneous. Energy is used to evaporate water only at the point of egress, permitting the nearly instantaneous delivery of heat in the form of warm mist.

The difference in scale between the present invention and humidifiers of the prior art thus offers improved safety relative to commercial warm mist humidifiers and steam vaporizers. The fact that relatively small volumes of water are heated for the near flash-generation of vapor avoids the over-humidification of the immediate environment occupied by a user and means that much lower levels of energy are required to vaporize liquids. Such techniques also avoid the increased growth of mold, dust mites, and other allergens observed in areas treated with broad-scale vaporizers. A localized, directed humidification mist can obviate many of the problems observed and associated with larger-scale vaporizers of the prior art. For instance, the inventive vaporizers described herein require less water than conventional room humidifiers and can be used in domestic, commercial, indoor, outdoor, fixed as well as portable settings.

An exemplary vaporization device of the present invention includes, at its heart, a heater and a porous member matingly configured for heat transfer between the heater and the porous member, in combination with a housing, a mechanical force generator, and a temperature modifier. The apparatus may also include optional elements such as a wick, a condensate return member, a liquid reservoir and a temperature modifier as well as additional elements or combinations of any of the foregoing, depending upon the desired use or purpose for the vaporizing apparatus. The configuration of the components in the instant invention is such that a directed flow of water vapor at elevated temperature is realized.

BRIEF DESCRIPTION OF THE DRAWINGS

FIG. 1 is a schematic cross section view of a capillary vaporizer according to co-pending and commonly assigned application for U.S. patent Ser. No. 12/095,481.

FIG. 2 is a schematic cross section view of the capillary vaporizer portion of a thin film vaporizer according to several aspects of the present invention.

FIG. 3 is a side sectional view of an exemplary thin film vaporizer device embodying several aspects of the present invention.

FIG. 4 is side schematic view of a condensation collar according to one aspect of the present invention.

FIG. 5 is a top schematic view of a condensation collar.

FIG. 6 is an oblique view of a condensation collar.

FIG. 7 is a schematic plan view showing the combination of a capillary vaporizer with a platform and a bowl in accordance with a further aspect of the thin film vaporizers of the present invention.

DEFINITIONS

In the present specification and claims, reference will be made to phrases and terms of art which are expressly defined for use herein as follows:

Directed water vapor as used herein refers to a characteristic of the inventive vaporizers to aim an aqueous vapor stream toward a target area of an individual such as a face, eye, nasal region, mouth, tracheostomy site, and the like. This may be achieved by using the device alone or in combination with a removable personal accessory. Personal accessories that are contemplated for use with the inventive vaporizers include facemasks, nose masks, eye pieces and exfoliation brushes. The fact that the method and devices of the present invention can provide directed water vapor is in contrast with broad-scale room humidifiers, which discharge water vapor to a much larger, general region.

Germ free as used herein means at least a 6-log reduction in microbes in vapor exiting an inventive device as compared to a level intentionally introduced into a water reservoir of the device for testing purposes.

Microbes is understood herein to refer to microscopic organisms and includes: bacteria, molds and fungi, archaea, and protists; microscopic plants also called green algae; and animals such as plankton, planarian and amoeba.

Over-humidification as used herein is understand to the describe the phenomenon of providing water vapor in surplus to a therapeutic need, with the result of providing a favorable breeding environment for such deleterious entities as dust mites, mold, and other allergens.

Reserved water energy, or $E_{RW}$, is defined as the amount of energy potentially available from a given mass of water, expressed in Joules or kilojoules. Reserved water energy may be calculated from Equation 1 below, where the specific heat capacity of water (C) is expressed in Joules per gram-° K; the mass of water (m) is expressed in grams (g); and the difference in temperature between the water ($T_1$) and the ambient environment ($T_2$) is expressed in degrees Kelvin (° K):

$$E_{RW}=Cm(T_1-T_2) \qquad \text{Equation 1}$$

For example, water has a specific heat capacity of 4.1855 J/g·° K. Sixty grams of boiling water therefore have a reserved water energy of: (4.1855 J/g·° K)×(60 g)×(373.15° K−293.15° K) or 20.1 kJ.

Safe heat as used herein refers to a range of temperatures that an individual would generally find comfortable. More particularly, as used herein, safe heat pertains to a range of temperatures from about 36° C. (96° F.), to about 49° C. (120° F.). These temperatures represent a range over which an individual would find the breathing of warm vapor from an inventive vaporizer to be comfortably acceptable.

Scalding is a burn injury caused by hot liquids or gases. Burns are caused by the skin's inability to dissipate energy; wherein outside energy is transferred into the skin at a rate higher than that at which it can be dissipated or eliminated by the body. While mainly limited to second-degree burns— that is, those characterized by blisters, clear fluid, and pain—in extreme circumstances scalding can result in third-degree burns, resulting in damage to deep or reticular dermis. Of the highest risk for suffering from scalding are young children and those over 65 years of age.

Secondary delivery as used herein relates to prior art humidifiers and vaporizers, which provide water vapor to a much larger space, general region or room. For example, water vapor generated by secondary delivery devices is first dispensed into a room before it can be safely and comfortably experienced by an individual. In general, the use of a removable personal accessory is neither provided nor recommended for use with such devices, as there are no provisions against scalding.

Vaporizer as used herein is understood to refer to a device for converting water or medicated liquid into a vapor for inhalation, according to its standard dictionary definition. In addition, vaporizer as used herein may also refer to a device for providing and supplying or maintaining humidity.

DETAILED DESCRIPTION OF THE INVENTION

Overall Configuration/Geometry

A thin film vaporizer according to the present invention may be regarded as comprising a capillary vaporizer or CV, a housing, a temperature modifier, an optional condensate collector or condensation return member, and an optional liquid feed system. The capillary vaporizer or CV further comprises a heating element and a porous member matingly configured for heat transfer between the heater and the porous member, in combination with a housing platform and a mechanical force generator. The platform provides a convenient structural element for engagement by the mechanical force generator, in order to provide compressive force between the porous member and the heating element. The porous member further comprises an insulator and an optional vaporization region. According to one embodiment, the heating element further comprises a heat trace provided on a heating substrate.

The housing platform and condensate collector may comprise either separable elements or a unitary component. According to one embodiment of the present invention, the platform and condensate collector are separate components. The platform may be a flat disk configured to accept an attachment means of the mechanical force generator. In one embodiment of the present invention, the platform includes a recess within which the porous member is seated. The platform recess has a height of less than 30%, preferably less than 20% and most preferably less than 10% of the height of the porous member. In another embodiment of the present invention, the height of the porous member is less than 3 cm, preferably less than 2 cm, and most preferably less than about 1 cm. Therefore, in one embodiment of the invention, the housing platform recess has a height of less than 3 mm preferably less than 2 mm, and most preferably less than 1 mm.

In a preferred embodiment, the capillary vaporizer or CV at the heart of the thin film vaporizer comprises a heating element, a porous member, a mechanical force generator and a housing. The inventive thin film vaporizers may also include optional elements such as a liquid reservoir, a wick, a condensation return member, means for turning the device on and off, electronic control means, as well as additional elements or combinations of any of the foregoing, depending upon the desired use or purpose for the vaporizer. The components of the instant invention are configured such that a directed flow of vaporized liquid at elevated temperature is realized.

One feature of the inventive thin film vaporizers that is distinct from prior art devices described above is that the boiling of aqueous liquids is confined to a small region and consequently a geometrically small volume of liquid. Heat sufficient to vaporize liquid feed is generated at a heat trace and provided by the heating element to an upper surface of the porous member. Thermal conduction imagery confirms that boiling takes place in the inventive vaporizers at the uppermost region of the porous member that lies in closest, heat-exchanging proximity to the heater substrate. This has given rise to the observation that the geometric configuration of liquid that is heated to vaporization may be described as a thin liquid film or simply a thin film. In fact, the quantity of liquid that is heated to boiling at any one time in the inventive vaporizers is less than about 5 g, preferably less than about 4 g, more preferably less than about 3 g, and most preferably less than about 2 g. The volume of liquid that is heated to boiling for vaporization at any point in time is therefore less than approximately 5 ml, preferably less than about 4 ml, more preferably less than about 3 ml, and most preferably less than about 2 ml.

The ability of the instant thin film vaporizers to quickly and efficiently heat small quantities of aqueous liquid to vapor is attributable, in part, to the configuration, geometry and materials used for the porous member and heater. For instance, the pore size distribution within the material used for the porous member is important, as discussed below. Also of importance are such factors as the evenness and flatness of the surfaces at which the porous member engages the heater. It has been found that during fabrication, some surface preparation is beneficial for the upper surface of he porous member and the lower surface of the heater in order to ensure good contact and therefore efficient heat transfer from the heater to the porous member. Techniques that have been found useful for providing a flat and smooth surface on the porous member and the heater include machining as by grinding and/or sanding. A particularly preferred type of surface preparation is known to those familiar in the art as lapping. It is preferred that the engaging surfaces of the porous member and heater surfaces are both very flat. In one aspect of the inventive thin film vaporizers, the flatness of the mating surfaces of the porous member and the heater are each measured to within tenths of a millimeters or ±0.1 mm (hundredths of an inch or ±0.01 in.) and preferably to within hundredths of a millimeter or ±0.01 mm (thousandths of an inch or ±0.001 in.). In a preferred embodiment, the flatness of the heater and porous member mating surfaces are made flat to within thousandths of a millimeter, that is, to within less than about 50 microns or 0.05 µm (±0.002 in).

Figure 2:
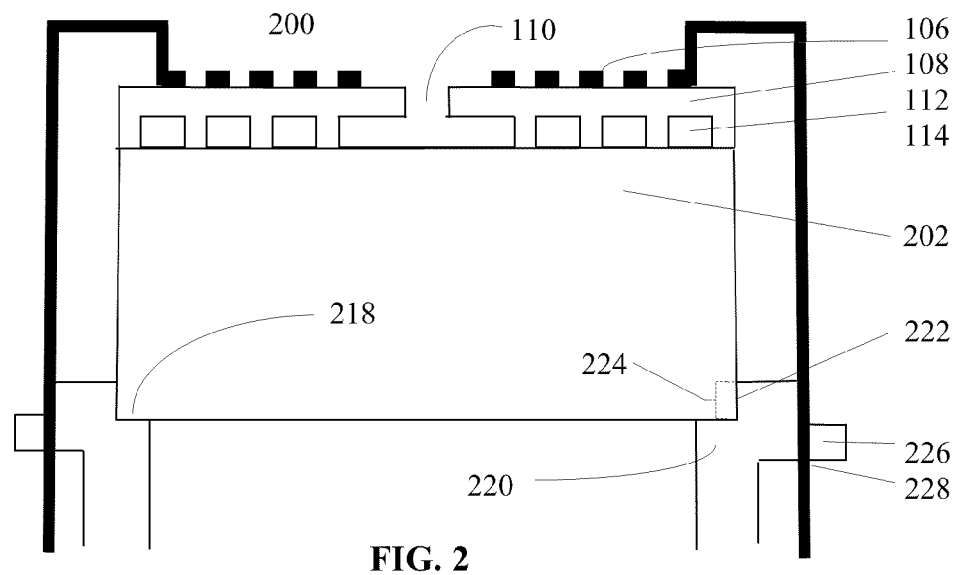

The following discussion can best be understood by reference to of FIGS. 1 and 2. As indicated above, the pore size and pore size distribution are important factors to consider in selecting a material for the porous member. Pore sizes needs to be small enough to permit the vapor generated from the porous member to collect and build pressure within vapor collection channels 112 situated between porous member 102 or 202 and heater 108, and thereby help force the generated vapor out through orifice 110. At the same time, the porous member needs to have pores that are sufficiently large so as to neither impede the desired level of liquid flow through the porous member, nor easily clog the porous member with impurities such as trace levels of salts or microbes. It has therefore been found advantageous that the pores of the porous member do not exhibit one uniform size. Rather, a distribution of pore sizes is preferred.

The selection of pore size distribution is particularly important when liquid feeds are used with the inventive thin film vaporizers, especially for those organisms that require exposure to elevated temperature for an extended period of time in order to be killed. The force with which water vapor exits a CV is sufficient to entrain trace levels of salts or microbes, even though neither salts or microbes boil. Therefore, it is important that the distribution of pore sizes include pores that are small enough to impede the progress of microbes as they move through the porous member. This impediment extends the residence time of microbes in the boiling region of the porous member, such that they can be destroyed by the heat of the boiling process. While most microbes remain as an impurity in the porous member, some will be ejected with the water vapor. Accordingly, it is important that these microbes are destroyed before they are ejected and ultimately inhaled by an individual. This is especially true for fungi, which generally require an extended period of exposure to heat at elevated temperature in order to be destroyed.

Fungi generally have physical sizes of 1 micron or greater. Therefore, it is important that at least 3%, preferably at least 4% and more preferably at least 5% of the pore sizes need to be 3 microns in size or less, in order to slow the progress of fungi through the porous member such that they can be boiled and destroyed prior to ejection from the device. According to one embodiment, the porous member of the inventive thin film vaporizers exhibits a wide distribution of pore sizes. However, the distribution of pore sizes within the porous member is such that the mean pore size is less than 25 microns, preferably less than 20 microns and more preferably less than 15 microns in size. It is preferred that the distribution of pore sizes include pore that are as small as 1 micron, such that certain microbes—such as molds—can be trapped and killed. In one embodiment of the invention, the porous member has a mean pore size of less than 15 microns. In a preferred embodiment, the pore size distribution also includes pore sizes of from 1-6 microns.

While the use of deionized or distilled water is especially preferred with the device and methods of the present invention, it is understood that even such sourcing of water can be infected or otherwise contaminated with microbes. Fortunately, however, the ability of the inventive devices to deliver germ-free aqueous vapor derives in part from its microporous componentry. Without being bound by theory, it is believed that judicious selection of the material used for the porous member as well as the size distribution of pore sizes in the porous member are important in providing a device that will exhibit desirable properties with respect to any germs and microbes that may be present in the feed liquid. Through careful selection of porous member material, the resultant tortuous path created therein can provide initial filtration of source liquids that are to be vaporized. Further, without being bound by theory, it is believed that the very nature of capillary force vaporization allows for momentary pressurization of the water vapor; essentially creating a miniature autoclave to provide efficient removal of microbes. As is shown below, the inventive apparatus has been found to be surprisingly capable of removing common pathogenic microbes, thus delivering a vapor that is essentially free of said microbes, even in the event of water source contamination.

An important feature of the thin film vaporizers of the present invention is that the bulk of any liquid feed that is used with the inventive vaporizers—for instance, any liquid that may be present in a liquid reservoir—remains at ambient temperature. This is due to the fact that the only heating that occurs in the inventive devices for purposes of vaporization is confined to the region in which the porous member contacts the heater. In this way, the potential for accidental scalding from contact with larger volumes of heated water is obviated with the inventive vaporizers. In addition, the fact that only very small volumes of liquid are heated to vaporization in the inventive vaporizers advantageously permits the nearly instantaneous generation of vapor. This is because only a thin layer of liquid need be heated to vaporization at any time. This, in turn, provides for novel heat delivery with the inventive vaporizers as compared to vaporizers or humidifiers in the prior art. The instant devices therefore efficiently deliver heat to an individual due to the fact that aqueous systems have such high heat capacities. Accordingly, a small amount of aqueous liquid can contain a sizeable quantity of heat. In a sense, therefore, the inventive devices may be regarded as providing tiny packets of water with the capacity for delivering a large quantity of heat. The level of heat may be easily and conveniently controlled in the inventive devices through the use of the temperature modifier, as described in greater detail below.

Accordingly, a device for the vaporization of liquid of the present invention may be regarded as including:

a) a porous member comprising an insulator and an optional vaporizer, the porous member also including a surface for receiving the liquid and an area for the pressurization of vapor that is produced from the liquid;

b) a heater for conveying heat to the porous member for vaporizing the liquid, the heater further including a vapor containment region for the collection of vapor and at least one orifice for release of the vapor at a velocity greater than zero;

c) a platform including a recess for engaging the porous member; and d) a mechanical force generator;

wherein the mechanical force generator is external to the porous member and the heater component and engages the platform in order to provide compressive force among the porous member and heater component.

Vaporizers of the instant invention may additionally comprise a liquid reservoir, a wick, a condensate collector, a temperature modifier, means for turning the device on and off, electronic control means, as well as additional elements or combinations of any of the foregoing, depending upon the desired use or purpose for the vaporizer. Additional examples and alternate embodiments of the present invention will be further elucidated through reference to the accompanying Figures and the following discussion.

An example of a capillary vaporizer, or CV, having a former configuration is shown schematically in FIG. 1 at 100, while FIG. 2 shows a schematic of a CV according to one embodiment of the present invention at 200. Note that like reference numbers are used throughout the figures to represent similar parts or features of the drawings. Turning first to FIG. 1, capillary device 100 comprises porous member 102 and optional insulator 104 for the delivery of liquid feed via capillary forces to a heater. The porous member is in intimate heat-exchanging contact with the heater, which further comprises heating element 106, heat exchanger 108, orifice 110 and vapor collection channels 112. Vapor that collects and becomes pressurized at vapor collection channels 112 situated at the interface between porous member 102 and the heater is released at orifice 110 at a pressure higher than the initial pressure at which the liquid feed is introduced to porous member 102. Electrical leads 114 connect heating element 106 to a power source (not shown).

Device 100 of FIG. 1 rests upon ledge 118 of housing 120 disposed towards the interior, and situated along the lower portion, of inner wall 122 of housing 120. Outer housing 116, which may comprise a variety of shapes and configurations, variously helps to provide an attachment, anchoring or containment point for a mechanical force generator embodied in electrical leads 114. In one aspect, the mechanical force generator including electrical leads 114 comprises a spring clip. Electrical leads 114 may further comprise a bead, tab, hook, or like feature for engaging outer housing 116. Note that inner housing 122 and outer housing 116 provide an alignment pathway for electrical lead 114.

In a prior art configuration of a capillary vaporizer 100 in FIG. 1, housing walls 122 of housing 120 were disposed at various distances remote from the porous member and heater components of 100, resulting in the inclusion of an opening or gap 124 therebetween. The inclusion of gap 124 afforded advantages in operability and longevity for device 100 over capillary force vaporizers of the prior art that were either enshrouded within a welded can-type enclosure or peripherally wrapped with an applied glazed coating material. For examples of the latter, see U.S. Pat. Nos. 6,126,046 and 6,634,864, both to Young, et al., respectively.

In a first embodiment according to the present invention, however, housing wall 122 is virtually gone, as indicated for capillary vaporizer 200 in FIG. 2. That is, housing platform 220 may optionally include a shallow recess such that porous member 202 is seated upon ledge 218 and rests against short inner edge 222 of platform 220. The height of inner edge 222 is exaggerated for clarity at 224 in FIG. 2. Note that providing an inner edge is not critical and is provided merely as a convenience for alignment during assembly of capillary vaporizer 200. Accordingly, height 224 of inner edge 222 is less than 30% of the height of the porous member, preferably less than 20%, and more preferably less than 10% of the height of the porous member. By way of example, for a sample porous member having a height of one centimeter (10 mm), the height of inner edge 222 would be less than 3 mm, preferably less than 2 mm, and most preferably less than 1 mm.

Housing platform 220 features an attachment means, anchoring means or containment means for engaging electrical leads 114. In one embodiment of the present invention, platform 220 includes an attachment means in the form of tab or cleat 226 that is provided either singly or in pairs (not shown) for engaging electrical lead 114 to platform 220. In one configuration according to the present invention, electrical lead 114 may also contain an anchor element 230 (not pictured) for engaging platform 220 at engagement point 228 of cleat 226. Where anchor element 230 is a cross-piece, tab 226 will comprise a pair of tabs for engagement of electrical lead 114. Where anchor element 230 is situated on only one side of electrical lead 114, tab 226 may only be present as a singular tab or attachment surface. As two electrical leads are typically required for each heater, the capillary vaporizers of the present invention include at least two tabs 226 in each of the inventive humidifiers, one situated at either end of a diameter of the capillary vaporizer. However, other configurations for heater trace 106 and electrical leads 114 are also possible, as will be apparent to those skilled in the relevant art. Note that the resulting arrangement for capillary vaporizer 200 is essentially an open configuration. That is, capillary vaporizer 200 has virtually no walls, peripheral seal or enclosure surrounding the capillary vaporizer. Surprisingly, it has been found that the key to being able to achieve this open configuration is attributable to providing sufficient compressive force among the capillary vaporizer components. Thus, tab 226 or a like anchoring means permits the use of a mechanical force generator capable of providing such necessary compressive mechanical force to hold the various capillary vaporizer components together, thus obviating the need for glazing, walls or containment means around the capillary vaporizer.

In light of the foregoing, therefore, a thin film vaporizer for the generation of pressurized vapor from unpressurized liquid in one embodiment of the present invention may comprise:

a) a porous member including an insulator and an optional vaporizer, the porous member also including a surface for receiving the liquid and an area for the pressurization of vapor that is produced from the liquid;

b) a heater for conveying heat to the porous member for vaporizing the liquid, the heater further including a vapor containment region for the collection of vapor and at least one orifice for release of the vapor at a velocity greater than zero;

c) a platform including an optional recess for engaging the porous member; and d) a mechanical force generator;

wherein the mechanical force generator is external to the porous member and the heater component and engages the platform in order to provide compressive force among the porous member and heater component.

According to another embodiment, a thin film vaporizer of the present invention may comprise:

a) a porous member including an insulator and an optional vaporizer, the porous member also including a surface for receiving a liquid to be vaporized and an area for the pressurization of vapor that is produced from the liquid;

b) a heater for conveying heat to the porous member for vaporizing the liquid, the heater further including a vapor containment region for the collection of vapor and at least one orifice for release of the vapor at a velocity greater than zero;

c) a platform including an optional recess for engaging the porous member;

d) a mechanical force generator;

e) a temperature modifier;

f) a means for supplying the liquid to the porous member; and g) a housing to contain elements a) through f);

wherein the mechanical force generator is external to the porous member and the heater component and engages the platform in order to provide compressive force among the porous member and heater component; and wherein the temperature modifier may be selected from among: baffles; a fan; a blower; vents; a compressed gas source; etc., as well as combinations of any of the foregoing.

According to another embodiment of the present invention, an inventive humidifier comprises a platform having a recess that includes a lip having a height that is less than 30%, preferably less than 20% and most preferably less than 10% of the height of the porous member.

Figure 3:
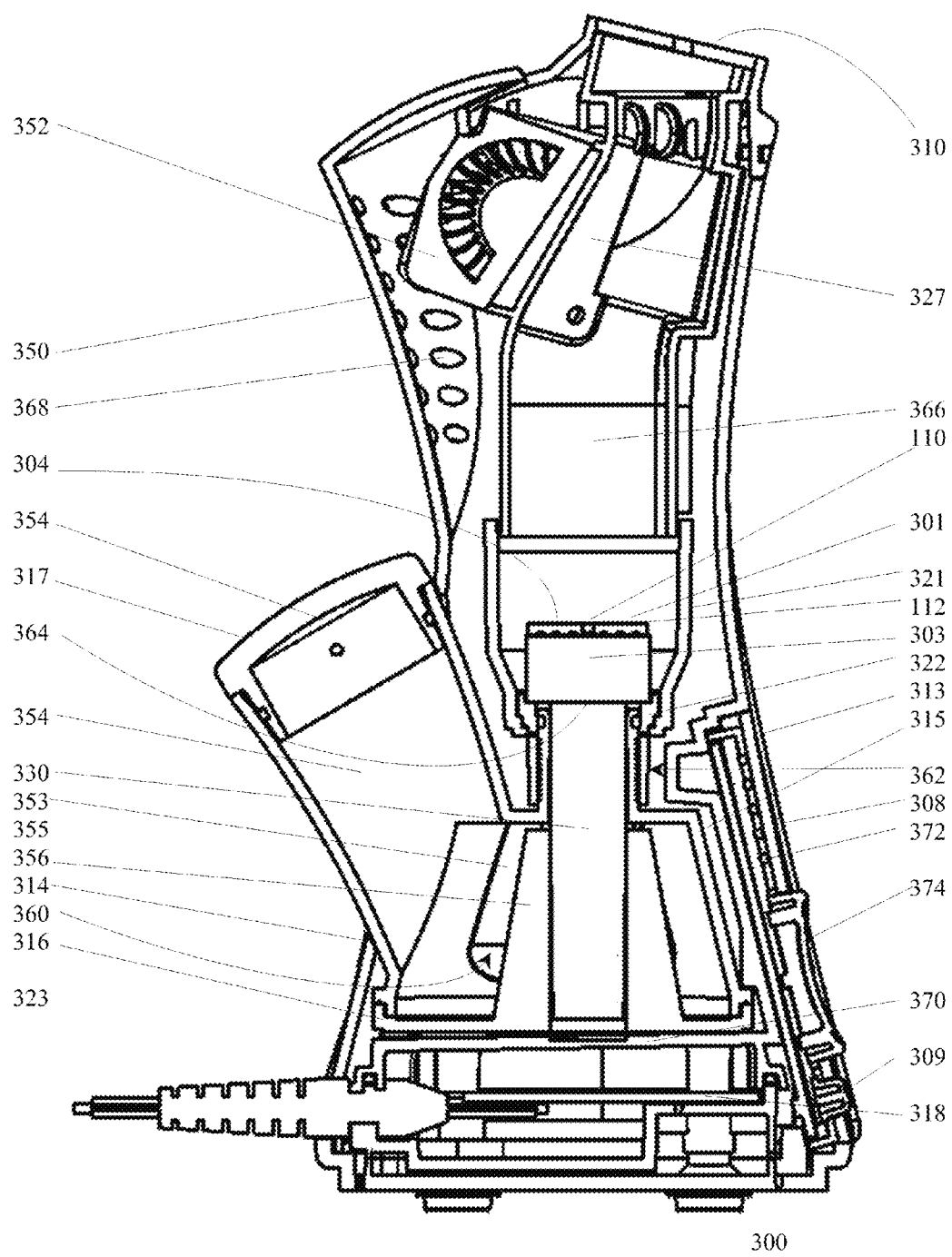

One configuration of a thin film vaporizer device in accordance with several aspects of the present invention will now be described with reference to FIG. 3, which shows a typical device at 300. A removable filler cap 317 of inlet 354 provided in device housing 350 permits the introduction of liquid feed into the device at opening 358. Liquid reservoir 353 for receiving the liquid feed, defined by reservoir bottom 316 and reservoir top 315, is shown in partial cut-away view at 355 to reveal a liquid level indicated at 360. In one aspect, liquid level 360 may be conveniently detected through a viewing port or window (not shown) in back panel 314 of device housing 350. Fins 356 of reservoir bottom 316 within reservoir 353 align and guide wick 330 towards first or lower surface 364 of the capillary vaporizer or CV portion of the device. Accordingly, guide means such as fingers or similar appropriate configuration at alignment guide 362 of platform 322 direct and position an upper end of wick 330 such that it matingly engages a first or lower surface 364 of porous member 303. Situated in heat-exchanging proximity with a second or upper surface of porous member 303 is heater or heat exchanger 304. Heat exchanger 304 includes heater element or heater trace 301 situated on a distal face from porous member 303 at an upper surface of heat exchanger 304. Together, porous member 303, heat exchanger 304 with heater trace 301, platform 322 and a mechanical force generator (not shown) that comprises spring clips 114 (shown schematically in FIGS. 1 and 2) comprise the capillary vaporizer or CV portion of device 300.

Platform 322 of the capillary vaporizer of device 300 matingly engages bowl 321, which leads to passageway 366. Vapor exiting the capillary vaporizer at orifice 110 passes through passageway 366 and proceeds towards the direction of device opening 310. In one aspect, the vapor exiting heat exchanger 304 at opening 110 first encounters temperature modifier 352 mounted at position or housing 327 prior to exiting device 300 at opening 310. For added safety, opening 310 may also optionally include projecting vanes, tabs or fingers 376 to prevent body parts such as fingers or other objects from being intentionally inserted into the device. Where temperature modifier 352 is a fan or blower, ambient air may be brought into device 300 at vent holes or openings 368 of housing 350. The mixture of ambient air entering device 350 from openings 368 and mixing with vapor from the capillary vaporizer prior to exiting device 300 enables the temperature of the vapor experienced at 310 to be adjusted as follows. Higher fan speeds bring in more cooling ambient air, resulting in a lower perceived vapor temperature above opening 310. A lower fan speed will bring in less ambient air, resulting in a lesser cooled or higher perceived vapor temperature above opening 310.

In order to adjust the relative temperature of vapor exiting device 300, control toggle or slide 374 is provided as part of user interface panel 308 on a front face 313 of device 300. In one aspect, power may be supplied to the device via power cord 323, which connects to a voltage source. Electronics (not shown) may be conveniently located in the device within a sealed compartment defined by vault top 370 and vault bottom 318 beneath reservoir 353. A series of signaling or indicator means such as lights may be provided at 372 such that they are viewable through user interface panel 308 in front 313 of housing 350. In one aspect of the invention, button 309 may be used to turn the power to device 300 on and off. In another aspect of the invention, slide 374 may be used to control the amount of power delivered to the device and thus control the speed of optional fan or blower 352, which in turn adjusts the relative temperature of vapor exiting the device at opening 310.

During normal operation of an inventive device in one aspect, liquid feed from reservoir 353 is delivered via an optional liquid supply means such as wick 330 to first face 364 of porous member 303. According to one embodiment, a porous member is in direct liquid communication with the liquid reservoir. According to another embodiment, a liquid supply means comprising a wick is used to conduct liquid from the liquid reservoir to the porous member. There, liquid is drawn by capillary action to an opposing face of the porous member where it approaches heat exchanger or heater 304. Heat from heat trace or heating element 301 of heater 304 causes liquid to boil at an upper surface of porous member 303 and be vaporized at interface regions 112 (for clarity, see FIGS. 1 and 2) between heater 304 108 and porous member 303 such that the quantity of liquid being vaporized at any time is best characterized as a thin film. Buildup of vapor then takes place at the heat exchanger-porous member interface, resulting in an increase in pressure of the vapor in collection channels 112 until such point that the vapor is propelled outward from heat exchanger 304 through orifice 110. The vapor is thus released at orifice 110 in the form of a plume at a pressure greater than that of the liquid feed.

In order to control the relative temperature at which a user of the inventive thin film vaporizers would perceive the vaporized liquid, a temperature modifier is provided according to a preferred embodiment of the invention. The purpose for the temperature modifier is to ensure that the temperature of vapor that is experienced by a user of the device is of a comfortable nature. It is desired that the vapor that is provided by the inventive vaporizers for use by an individual should be neither too cold nor too hot. That is, the vapor should be made available at a comfortable temperature or within a safe heat range of temperatures. Accordingly, temperature modifiers may include such components as: a mouthpiece or nosepiece that induces mixing of vapor and air; compressed gas; a rotating member such as a blade or vane; a fan; baffles or other means to mechanically admix ambient air with vapor generated by the capillary vaporizer; as well as combinations of any of the foregoing. According to a one embodiment, the temperature modifier is a series of baffles. In a preferred embodiment, the temperature modifier is a fan or blower as indicated at 352 in FIG. 3. By increasing or decreasing the power to the fan, the fan can be made to work faster or slower, thus admixing more or less air, respectively, with the plume of vaporized liquid. As a result, the relative temperature at which vapor is delivered by the humidifier may be conveniently adjusted. That is, greater power to the fan results in more ambient air admixing with the vaporized liquid to lower the perceived temperature of the emitted vapor to a greater extent in a first instance. Less power to the fan results in the admixing of smaller quantities of ambient air with the vaporized liquid in a second instance, thus lowering the perceived temperature of the emitted vapor to a lesser extent. The result is that a warmer vapor plume is experienced by an individual in the second instance as compared to the perceived temperature of the vapor plume experienced by an individual in the first instance.

Condensation Collar; Temperature Modifier

Additional components that are suitable for use with the inventive vaporizers of the present invention include: a power supply means; power control means and associated electronics; a mechanism for turning the device on and off; a vapor condensation collector or condensate collar; signaling means to indicate the level at which the device is operating; a so-called "thermal fuse" to turn off the device in the event that it has run out of liquid feed and the software fails to turn off power to the device; electronics and/or microprocessors along with any associated software programs, controls or control programs for the operation and control of the device; as well as combinations of any of the foregoing.

The purpose for a condensation collar is to collect and channel any un-vaporized liquid feed condensate back to the active region of the capillary vaporizer for vaporization. Where water or aqueous compositions are used, the condensation collar provides a surface upon which moisture collects and can be returned to the porous member portion for re-vaporization. This is especially useful for those configurations of the inventive vaporizers in which a temperature modifier is situated distally from the outlet of the device, with the capillary vaporizer (CV) portion located therebetween. In such configurations, a temperature modifier can permit air movement towards the exit of the device, while still controlling the return of any condensed liquid. In addition, the condensate return system helps to prevent the contaminating of any remaining internal components of the humidifier and minimizes the chances that the electronics of the inventive humidifiers could be negatively impacted. Of primary importance is that any heated liquid be returned to the CV for vaporization in order that it not prove problematic for a user. Such is often not the case with current warm mist humidifiers.

Figure 4:
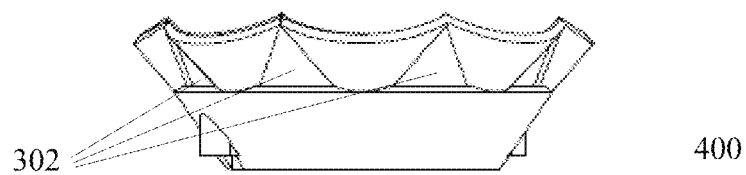
Figure 5:
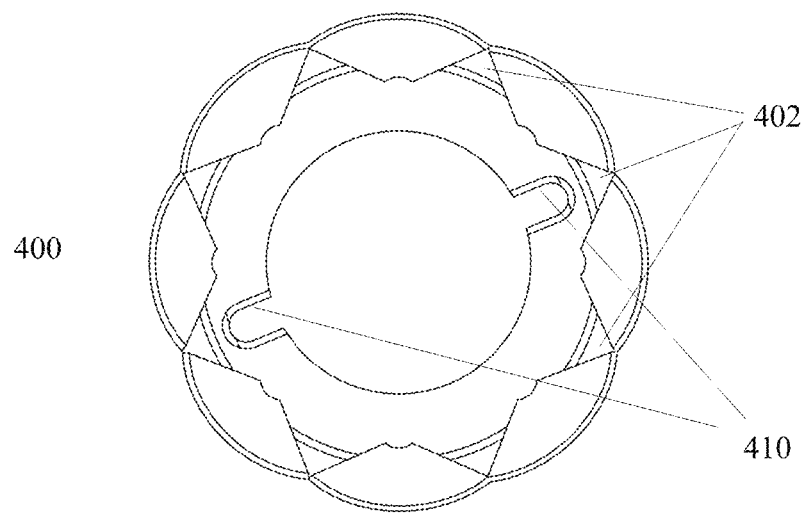
Figure 6:
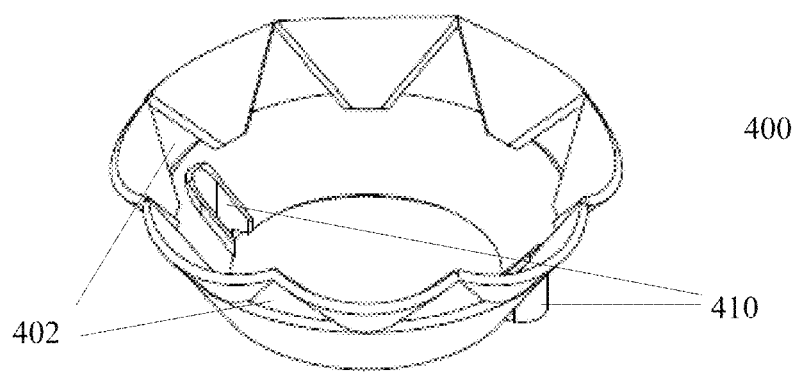

An example of one configuration for an optional vapor condensation collector or condensate return system according to one embodiment of the invention is shown in different perspectives at 400 in FIGS. 4, 5 and 6. Note that optional collector 400 of FIGS. 4-6 includes fluted sides that contain a plurality of vents or openings 402 for the through-passage of air. As will be understood by those knowledgeable in the relevant art, the configuration of collector 400 is not critical and at least one portion of collector 400 may be fluted as shown, as well as folded, corrugated, pleated, smooth, wavy, flat, as well as combinations of any of the foregoing. A pair of openings 114 for electrical leads to pass through collector 400 to connect with a power source are also shown at locations 410 in FIG. 5. According to one embodiment of the inventive vaporizers, openings 114 are located at diametrically opposed positions around optional collector 400.

For a preferred embodiment of the present invention in which a temperature modifier is situated between the device outlet and the CV, it has been found that a separate, vented collector for channeling liquid condensate back to the porous member for vaporization is not necessary. Such is the case when a fan is used as the temperature modifier. By situating the fan such that air is directed to sweep across orifice 110, it has surprisingly been found that there is essentially no incomplete vaporization, especially when aqueous liquids are used with the present invention. In such instances, it is therefore not essential to include a separate, vented condensation collector as one of the components of the inventive vaporizers. In such instances, a housing means such as bowl 730 may serve a dual purpose: contain the CV portion of the inventive thin film vaporizers and also prevent any extraneous vapor from condensing at unwanted points of the device. According to a preferred embodiment, bowl 730 is included with the inventive thin film vaporizers. Note that bowl 321 of device 300 of FIG. 3 is an equivalent element.

Figure 7:
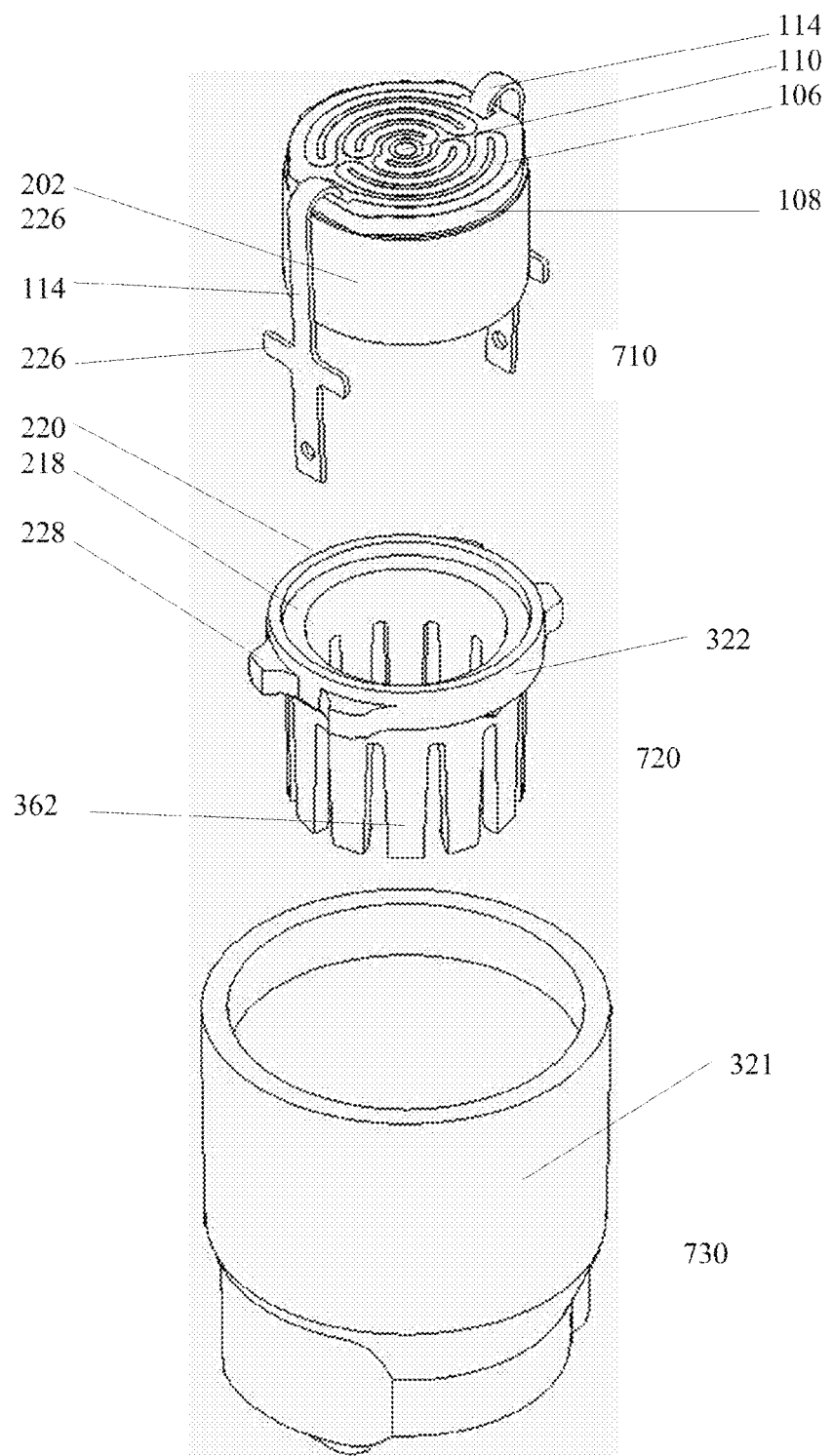

An assembly of the key components for a thin film vaporizer according to one embodiment of the present invention is shown in exploded view in FIG. 7. FIG. 7 shows a porous member, heater and mechanical force generator comprising a capillary vaporizer at 710, a platform at 720, and a bowl at 730. Note that the downwardly-extending fins of platform 620 have been found to be useful for purposes of alignment when a liquid delivery means, such as a wick, are included with the inventive vaporizers. The simplicity of essential components and the fact that very few mechanical parts are required have enabled development of the inventive vaporizers into small, compact and readily transportable devices. The inventive vaporizers readily lend themselves to being hand-held for use, if desired. In one configuration of a vaporizer according to the present invention, therefore, it has been found that a combination of heater and porous member together may occupy a volume less than 20 cm$^3$ (1.2 in$^3$), preferably less than 15 cm$^3$ (0.9 in$^3$), and more preferably less than 10 cm$^3$ (0.6 in$^3$) in size. In one embodiment of the present invention, the heater and porous member together may occupy a volume of up to 17 cm$^3$ (1 in$^3$). In another embodiment of the present invention, the heater and porous member together occupy a volume of less than 9 cm$^3$ (0.6 in$^3$).

Interestingly, it has been found with the thin film vaporizers of the present invention that even when using a heater-porous member combination that occupies a volume as small as on the order of 10 cm$^3$, it is possible to vaporize water at surprisingly high rates. Thus, vaporization rates as high as 2.0-2.5 g/min for water have been realized for thin film vaporizers according to the present invention in which the main components of the CV portion—that is, heater and porous member—had a physical size no greater than 25 mm in diameter with a combined height of 15 mm. However, processing on the order of 2.0-2.5 g/min water through an inventive device—although possible to achieve—is not desirable in practice. A much larger temperature modifier such as a blower or fan would be required to cool such large quantities of water vapor to the point that they would be comfortable to a user of the device. In order to provide a convenient and portable hand-held device, such larger temperature modifiers are not included with the inventive devices. Accordingly, the electronics of the inventive thin film vaporizers are set such that a convenient range of temperatures may be realized for aqueous feed that is vaporized by the device at a rate of not greater than 2.0 g/min, preferably not greater than 1.8 5/min and more preferably not greater than 1.6 g/min. According to several aspects, thin film vaporizers of the present invention vaporize aqueous feed at the rate of approximately 1.0-1.5 g/min.

Wick

During the operation of a thin film vaporizer according to the present invention, a liquid delivery system may be used to conduct liquid feed from a liquid reservoir to the porous member of the capillary vaporizer, as discussed above. In prior art capillary devices, the wicking member was often fashioned from various materials that had relatively small pores. Ceramics were one particularly preferred class of materials, especially for use with non-aqueous liquids. It was postulated that the smaller pores in many ceramics would result in higher capillary pressures realized in the wicking member. It was felt that higher capillary pressures, in turn, would result in the ability to generate greater vapor pressures upon vaporization of the liquid, while simultaneously preventing excessive heat and/or vapor from migrating from the heater towards the feed direction of the liquid. However, the pores of many of these wicking members were too small, resulting in unacceptably higher capillary forces. Unfortunately, the wicking members that tended to exhibit higher capillary forces were also found to essentially transmit liquid feed at insufficient rates, in addition to the fact that they were expensive and difficult to manufacture. That is, the rate of delivery of the liquid feed to the capillary member for vaporization was too low, resulting in an insufficient vapor pressure of the released vapor from at the heater orifice.

Surprisingly, it has now been found that wicks or wicking members made of organic materials can be used with the instant thin film vaporizers. The principal features that are considered in selecting a wicking member are fluid transport and thermal properties, in addition to mechanical strength and integrity. When the inventive device is used with aqueous systems, the fluid transport properties that should be considered include, at least in part, to the ability of the wick to efficiently conduct water or aqueous liquids from a reservoir to the porous member. In such applications, the hydrophilicity of the wick should be taken into account. Thermal properties such as the resistance to melting, charring, or other thermal degradation should also be considered.

Also somewhat surprisingly, it has been found that certain organic materials can actually provide advantageous wicking properties over many ceramics as wicking members when used with the inventive thin film humidifiers. Examples of suitable organic materials that can be used as a wicking member with a thin film humidifier of the present invention include, but are not limited to: polyester; nylon; cellulose; acetate; cellulose acetate; blends of any of the foregoing; as well as combinations of any of the foregoing.

For non-aqueous systems, polyester and other hydrophobic materials are preferred for use as a wicking member with thin film vaporizers of the present invention. However, for aqueous systems, polyester and other hydrophobic materials are not preferred. Interestingly, in several trials in which non-hydrophilic fibers were coated with a surfactant to increase the hydrophilicity of a wicking member, two disadvantages were observed. The wicks not only demonstrated a loss of hydrophilicity over time, but the heater orifices of the inventive thin film vaporizers experienced the build-up of clogging material. Nylon, a naturally hydrophilic substrate, has been found to be more acceptable as a wicking material.

Nylon alone, however, lacks certain inherent mechanical strength that has been found to be beneficial for the wicking member. For instance, the wick must be pressed with a good amount of force to a lower surface of the porous member in order to efficiently conduct fluid from a fluid reservoir to the porous member to be vaporized. Moreover, the incorporation of a elements with good mechanical strength are preferred to ensure the maintenance of compressive force and efficient fluid delivery throughout the life of the device. A number of techniques were therefore evaluated for possible use with nylon fibers in order to increase the mechanical strength of the wick. Examples of such techniques include: incorporating stiff fibers of a second, mechanically stronger material into the wick; using plastic or metal rods within a wick; using an exterior mesh system to hold a wick in place; employing a plastic wrap; using of a plastic sleeve; and so forth. Because the wick of the inventive thin film vaporizers is not exposed to heat, is not heated and is not exposed to steam, one could theoretically use any material to bolster the mechanical strength of the wick. Somewhat interestingly, therefore, it was found that a mixture of fibers of nylon with fibers of a second, mechanically strong material has resulted in the generation of an improved wicking member. Mechanically strong materials that may be interspersed among nylon in order to generate a more robust wicking member include: polyester, polyethylene terephthalate, graphite, plastic and polyethylene. Accordingly, it has been found that the wicking member of the inventive thin film vaporizers may comprise a blend of up to 50% of a material having better mechanical strength than nylon, preferably up to 40% and more preferably up to 30% of a material having a better mechanical strength than nylon. According to another embodiment, a wicking member for use with the inventive thin film vaporizers comprises 60-90% nylon with the remaining 40-10% of the wick comprised of polyethylene terephthalate. A wicking member for use with the inventive thin film vaporizers according to a preferred embodiment contains 70% nylon fibers and 30% polyethylene terephthalate fibers.

Low Energy Requirements and Reserved Water Energy

The thin film vaporizers of the instant invention are distinct from many devices of the prior art in that they enable the delivery of heat and moisture in the form of directed water vapor to a user of the device. Directed water vapor as used herein refers to a characteristic of the inventive vaporizers to aim an aqueous vapor stream toward a target area of an individual such as a face, eye, nasal region, mouth, tracheostomy site, and the like. This may be achieved by using the device alone or in combination with a removable personal accessory. Personal accessories that are contemplated for use with the inventive vaporizers include face masks, mouth pieces, eye cup pieces, nasal canulas and nose masks. The fact that the method and devices of the present invention can provide directed water vapor is in contrast with broad-scale room humidifiers, which discharge water vapor to a much larger, general region and provide no such directed benefit to an individual.

Using a thin film vaporizer of the present invention, it has now been found that it is possible to produce water vapor within less than about one minute of applying power to the device. The thin film vaporizers of the present invention have been found to be suitable for use where the delivery of aqueous vapor is desired within less than 45 seconds of applying power, preferably less than 30 seconds of applying power and more preferably less than 15 seconds of applying power. According to one embodiment of the present invention, delivery of aqueous vapor to an individual is achieved in less than 5 seconds. According to another embodiment of the present invention, delivery of aqueous vapor to an individual can be achieved in less than 3 seconds.

EXAMPLES

Example 1

The reserved water energy of several commercial warm mist devices was calculated and compared to the inventive device. Accordingly a Mabis Steam Inhaler Model 40-741-000 was found to hold approximately 80 ml of water, which was introduced to the device at approximately 20° C. Boiling was effected within about 2.5 minutes of power being applied. The water therefore had a reserved water energy of 4.1855 J/g·° K×80 g×(373.15° K−293.15° K)=26.8 kJ. A Vicks® Personal Steam Inhaler Model V1200 was found to hold approximately 75 ml of water, which was also introduced to this device at 20° C. Boiling was effectuated within 10 minutes of power being applied. At this point, the water had a reserved water energy of 4.1855 J/G·° K×75 g×(373.15° K−293.15° K)=25.1 kJ. A Walgreens Personal Cough & Cold Steam Inhaler, Model FSA88 (Item Number 809729) was found to hold approximately 60 ml of water, which was also introduced at 20° C. Boiling was effectuated within about 5 minutes of power being applied. The water therefore had a reserved water energy of 4.1855 J/g·° K×60 g×(373.15° K−293.15° K)=20.1 kJ.

A thin film vaporizer according to the present invention was filled with 40 ml of water at 20° C. Steam generation was affected within five seconds of power being applied, and the unit was allowed to produce steam for 4 minutes. At the end of 4 minutes' time, it was found that the amount of water that was present in the porous member weighed approximately 1.3 g. If all of the 1.3 g of water were to have achieved a temperature of 100° C., the reserved water energy for the 1.3 g can be calculated as follows: 4.1855 J/g·° K×1.3 g×(373.15° K·293.15° K)=0.4 kJ. In fact, it has been determined that the quantity of liquid that is heated to vaporization at any time using the inventive thin film vaporizers, is approximately 0.1 g, thus giving rise to a reserved water energy of 0.03 kJ. Accordingly, a thin film vaporizer of the present invention may be characterized as a device that produces less than 20 kJ reserved water energy, preferably less than 15 kJ reserved water energy and more preferably less than 10 kJ reserved water energy. According to one embodiment, the thin film vaporizers of the present invention have a reserved water energy of less than 1 kJ. In another embodiment, the thin film vaporizers of the present invention have a reserved water energy of less than 0.5 kJ.

While any scalding injury is to be avoided, the American Burn Association prescribes that should 10% of the total body surface area (TBSA) be exposed to a burn, the victim should seek specialized medical attention at a burn center. See, for instance: University of Chicago Medical Center, http://www.uchospitals.edu/online-library/content=P01146; American Burn Association and American College of Surgeons, 1999; "Resources for the Optimal Care of the Injured Patient," Committee on Trauma, American College of Surgeons, pp 55-62. Further, as an estimate of the extent of a burn, the so-called "Rule of 9" established by Wallace (Wallace A. B. 1951. "The Exposure Treatment of Burns", Lancet, 1, 501-504) provides guidance:

| Area | % TBSA |
|---|---|
| Head | 9% |
| Each upper limb | 9% |
| Each lower limb | 18% |
| Front of trunk | 18% |
| Back of trunk | 18% |
| Perineum | 1% |

One method of estimating body surface area (or BSA; see Mosteller R. D, 1987. "Simplified Calculation of Body Surface Area," *N. Engl. J. Med.* 1987; 317(17):1098) is provided by the formula given in Equation 2 below:

$$BSA(m^2) = ([Height(cm) \times Weight(kg)]/3600)^{1/2} \qquad \text{Equation 2}$$

For a two-year old child in the U.S., the average height is about 34 cm and the average weight is 12.5 kg, giving an average BSA or body surface area of 0.12 m². Ten percent of this BSA would be approximately 0.012 m². A water layer of 5 mm over 10% BSA for an average two year-old would thus constitute 59 ml (0.2 oz or 0.25 cup). In other words, as little as 59 ml (0.2 oz) of scalding water would likely result in burns over 10% of an average two year-old child's body, which would mandate specialized medical attention. The reserved water energy of 59 ml would be 19.8 kJ. It should be noted that the thin film vaporizers of the present invention, with less than 1 kJ reserved water energy therefore offer nearly a 20-fold reduction in scalding hazard. In light of the 60 ml to 80 ml boiling water capacity of the prior art devices mentioned above, therefore, the inventive thin film vaporizers offer a distinct margin of safety.

Disinfection

In the course of testing and evaluating thin film vaporizers according to the present invention, it was repeatedly found that the instant vaporizers permit the production of vapor free from microbes. Without being bound by theory, it is believed that the ability of the inventive devices to ensure germ-free water vapor derives in part from its microporous componentry and the distribution of pore sizes in the porous member, as discussed above. Another factor in the ability of the inventive thin film vaporizers to eliminate any mold and bacteria that might be introduced to the device along with the feed liquid concerns the temperature modifier. In particular in instances in which the temperature modifier is a fan, the fan can be used to eliminate moisture from the device by continuing to run after power to the heater has terminated. This is a feature that can be included in the control circuit for the device, as will be understood by those knowledgeable in the relevant art, and is discussed in greater detail below.

Studies were conducted to evaluate the ability of the inventive vaporizers to prevent transmission of microbes in the mist when such microbes were intentionally introduced to the inventive thin film vaporizer with the liquid feed. Various prior art room humidifier products were also tested in the same manner. Solutions of bacteria and fungi were prepared and introduced into the liquid feed water supply as described for all products tested.

Example 2

Eight commercially available humidifiers were evaluated for efficacy against both bacteria and fungus and the results were compared to the performance of a thin film device according to the present invention. The prior art room humidifier devices that were used are listed here and summarized in Table 1, along with the type of mist generated—designated either cool or warm—and any mechanisms used to control germs. The prior art room humidifier devices that were used were: 1) a Vicks® Model V745A warm mist humidifier; 2) a BROOKSTONE Germ-Free Humidifier with UV Sanitizing, a cool most humidifier that includes a UV light; 3) a Kaz HWLV790, an ultrasonic cool mist humidifier that includes a UV light; 4) a HONEYWELL HCM-350 Germ Free Humidifier, an ultrasonic cool mist humidifier that includes a UV light; 5) a PLASTON Air-O-Swiss Model 7135, a cool mist humidifier with silver ion technology to control microbes; 6) a WACHSMUTH & KROGMANN Crane® EE series ultrasonic cool mist humidifier; 7) a Vicks® Model V4500 cool mist humidifier with an impeller; and 8) a Vicks® Model V5100N ultrasonic cool mist humidifier. Each commercial device was used in accordance with its respective instruction manual. The bacteria and the fungus that was used for evaluation and testing purposes are given in Table 1.

Test samples were prepared as follows. Bacterial test water was prepared by adding a few loopfuls of the listed test bacteria into 1 L of sterile deionized water until a McFarland 0.5 concentration was reached. This was repeated in order to provide 2 L of bacterial test water. The bacterial test water was then added to each humidifier. Each device was then individually placed in a biological hood and allowed to run for 4 minutes. This was followed by placing a Tryptic Soy Agar (TSA) plate over the discharged steam for 2 min, followed by two more steam collections on a Petri dish for a total of three collections. Afterwards, a surface plate was taken from the opening where the steam exited each device. All TSA plates were then incubated at 35° C. for 24 hours. This was repeated for each device tested. Bacteria that were used for testing were: *Pseudomonas aeruginosa, Salmonella choleraesuis, Cladosporium cladosporioides, Staphylococcus aureus, Escherichia coli, Moraxella* (Branhamella) *catarrhalis, Haemophilus influenza* and *Streptococcus pneumonia*.

A stock sample containing the fungus (mold) to be tested was prepared by inoculating four Modified Cellulose Plates and allowing them to incubate for 7 days at 28° C. Spores were then collected by adding 10 mL to each plate and scraping the spores with a sterile plastic loop. The 10 mL were then transferred into one of two 1 L bottles of sterile deionized water. New humidifiers were used to test molds so that contamination by bacteria was avoided. Each humidifier was then prepared and tested as mentioned above. Afterwards the steam produced by each humidifier was captured using Malt Extract Agar (MEA) for 2 min, followed by two more steam collections on a Petri dish for a total of three collections. Afterwards, a surface plate was taken from the opening where the steam exited the humidifier. All MEA plates were then incubated at 28° C. for 4 days. This was repeated for each humidifier being tested. After incubation, the agar plates were analyzed and results calculated. All tests were completed in triplicate. Molds that were tested were: *Cladosporium cladosporioides* and *Aspergillus nigerii*. The results obtained for bacterial and fungus studies are reported in Table 1 below.

germ tested. According to U.S. government standards, these products “disinfect” water feed as it is converted into vapor. It should be noted that while both the present invention and the Vicks® Model 745A effectively reduce germs, only the present invention reduces germs without posing a scalding hazard to its users.

The next best level of performance is seen by the ultraviolet light-equipped humidifiers. These units do not “disinfect” the mist, but do meet the definition of a “sanitizer,” as they reduce the germ load to at least a 4-log or 99.99% level. The product that relies on silver ion technology was found to not reduce germs. According to the results summarized in Table 1 above, silver ion technology appears to offer no protection against transmission of pathogenic germs. The non-UV light equipped cool mist humidifiers also showed surprisingly high levels of microbes. Cool mist humidifiers that are not equipped with an ultraviolet light capability offered a limited measure of germ transmission control and may therefore pose a germ transmission risk to users.

As the results from Table 1 above indicate, the inventive thin film vaporizers have been shown to be surprisingly

TABLE 1

PATHOGENIC TESTING RESULTS

| No. | Device | Description | Pathogen | Reduction of germs (%) |
|---|---|---|---|---|
| 1. | Present invention | Thin film warm mist vaporizer | Mold - *C. cladosporioides* | 99.99997% |
| | | | Bac. - *P. aeruginosa* | 99.999999% |
| | | | Bac. - *S. choleraesuis* | 99.999999% |
| | | | Bac. - *Staph. aureus* | 99.99998% |
| | | | Bac. - *Moraxella catarrhalis* | 99.99999% |
| | | | Bac. - *Haemophilus influenza* | 99.99999% |
| | | | Bac. - *Streptococcus pneumonia* | 99.99999% |
| 2. | Vicks ® V745A | Warm mist room humidifier | Bac. - *Staph. aureus* | 99.99999% |
| | | | Bac. - *Moraxella catarrhalis* | 99.99999% |
| | | | Bac. - *Haemophilus influenza* | 99.99999% |
| | | | Bac. - *Streptococcus pneumonia* | 99.99999% |
| 3. | Brookstone Germ Free Humidifier with UV | Cool mist ultrasonic humidifier with UV light | Bac. - *P. aeruginosa* | 99.99% |
| | | | Bac. - *Staph. aureus* | 99.99% |
| | | | Bac. - *E. coli* | 99.99% |
| | | | Mold - *A. nigerii* | 99.99% |
| 4. | Kaz HWLV790 | Ultrasonic cool mist with UV light | Bac. - *P. aeruginosa* | 99.99% |
| | | | Bac. - *Staph. aureus* | 99.99% |
| 5. | Honeywell HCM-350 Germ Free Humidifier | Ultrasonic cool mist with UV light | Bac. - *P. aeruginosa.* | 99.9% |
| | | | Bac. - *Staph. aureus* | 99.9% |
| 6. | Air-O-Swiss 7135 | Ultrasonic cool mist humidifier w/ silver ion | Mold - *C. cladosporioides* | TNTC |
| | | | Bac. - *Staph. aureus* | TNTC |
| 7. | Crane ® EE Series | Ultrasonic cool mist humidifier for children | Mold - *C. cladosporioides* | TNTC |
| | | | Bac. - *Staph. aureus* | TNTC |
| 8. | Vicks ® V4500 | Cool mist room humidifier | Bac. - *Staph. aureus* | TNTC |
| | | | Bac. - *Moraxella catarrhalis* | TNTC |
| | | | Bac. - *Haemophilus influenza* | TNTC |
| | | | Bac. - *Streptococcus pneumonia* | TNTC |
| 9. | Vicks ® V5100N | Ultrasonic cool mist room humidifier | Bac. - *Staph. aureus* | TNTC |
| | | | Bac. - *Moraxella catarrhalis* | TNTC |
| | | | Bac. - *Haemophilus influenza* | TNTC |
| | | | Bac. - *Streptococcus pneumonia* | TNTC |

Abbreviations used in Table XYZ:
UV = ultraviolet
Bac. = Bacteria
TNTC = too numerous to count. The number of living microbes was in the millions; too many to count.

As shown in Table 1 above, the inventive humidifier and the Vicks® 745A demonstrated nearly a complete reduction in the discharged steam of all bacteria and fungi tested, while all other devices transmitted germs to one degree or another. Both the Vicks® Model 745A humidifier and the thin film vaporizers of the present invention use a boiling mechanism to make vapor; both were found to achieve a 6-log or 99.9999% reduction in pathogens or better, depending on the capable of removing common pathogenic microbes, thus delivering a vapor that is essentially free of such microbes, even in the event of water source contamination. Accordingly, the devices of the present invention may be characterized as thin film vaporizers that cause at least a 4-log reduction, preferably a 5-log reduction, more preferably a 6-log reduction and, in certain instances, an 8-log reduction of microbes from aqueous feed as compared to emitted vapor.

The present invention has been described above in detail with reference to specific embodiments, Figures, Table and Examples. These specific embodiments should not be construed as narrowing the scope of the invention, but rather as illustrative examples. It is to be further understood that various modifications and substitutions are anticipated and may be made to the described vaporization devices and apparatus, as well as to materials, methods of manufacture and use, without departing from the broad spirit or scope of the invention contemplated herein. The invention is further illustrated and described in the claims, which follow.

What is claimed:

1. A portable vaporizer device for the generation of pressurized vapor from unpressurized liquid, comprising:
    a) a porous member comprising an insulator, the porous member also including a surface for receiving the liquid and an area for the pressurization of vapor that is produced from the liquid;
    b) a heater for conveying heat to the porous member for vaporizing the liquid, the heater further including a vapor containment region for the collection of vapor and at least one orifice for release of the vapor at a velocity greater than zero;
    c) a platform including a recess for engaging the porous member; and
    d) a mechanical force generator;
    wherein the mechanical force generator is external to the porous member and the heater and engages the platform in order to provide compressive force among the porous member and the heater.

2. The vaporizer of claim 1, wherein the platform recess has a height of less than 30% of the height of the porous member.

3. The vaporizer of claim 1, wherein the platform recess has a height of less than 3 mm.

4. The vaporizer of claim 1, wherein a configuration of liquid that is vaporized may be characterized as a thin film.

5. The vaporizer of claim 1, wherein at least one surface of either the porous member or the heater exhibits a flatness that is measured to tenths of a millimeter (hundredths of an inch).

6. The vaporizer of claim 1, wherein the porous member has a mean pore size of less than 25 microns.

7. A thin film vaporizer for generating pressurized vapor from unpressurized liquid, comprising:
    a) a porous member comprising an insulator, the porous member also including a surface for receiving the liquid and an area for the pressurization of vapor that is produced from the liquid;
    b) a heater for conveying heat to the porous member for vaporizing the liquid, the heater further including a vapor containment region for the collection of vapor and at least one orifice for release of the vapor at a velocity greater than zero;
    c) a platform including a recess for engaging the porous member; and
    d) a mechanical force generator for providing compressive force among the porous member and the heater;
    wherein the porous member and heater together occupy a volume of less than 20 cm$^3$.

8. The thin film vaporizer of claim 7, further comprising:
    e) a condensation collector;
    wherein the mechanical force generator is external to the porous member and the heater component and engages the platform in order to provide compressive force among the porous member and heater component; and
    wherein a surface of the condensation collector has a conformation that may be selected from among: corrugated, fluted, flat, folded, pleated, smooth, wavy and combinations of any of the foregoing.

9. A thin film vaporizer according to claim 7, having a heater and porous member that together are not greater than 25 mm in diameter and have a combined height not greater than 15 mm that is capable of vaporizing at least 2.0 g/min water.

10. The vaporizer of claim 1, further comprising:
    e) a wicking member for delivering the unpressurized liquid to the porous member for vaporization;
    wherein the wicking member is comprised of nylon together with up to 50% of a second material, the second material selected from among: polyethylene terephthalate, polyester; cellulose acetate; blends of any of the foregoing; and combinations of any of the foregoing.

11. The vaporizer of claim 10, wherein the wicking member is comprised of 60-90% nylon and 40-10% polyethylene terephthalate.

12. The portable vaporizer device of claim 1, wherein the reserved water energy of the portable device is less than about 20 kJ.

13. The device of claim 12, further wherein during normal operation, the opportunity for scalding due to exposure to boiling liquid is essentially nonexistent.

14. The device of claim 12, wherein the device is capable of producing directed water vapor within less than about 45 seconds of applying power to the device.

15. A method for generating pressurized vapor from an unpressurized liquid, comprising:
    a. providing a liquid feed to a portable vaporization device, the liquid characterized as having a first pressure; and
    b. vaporizing thin films of the liquid to produce a vapor, the vapor characterized as having a second pressure;
    wherein the second pressure is greater than the first pressure;
    wherein the portable vaporization device comprises a porous member, a heater and a mechanical force generator for providing compressive force among the porous member and the heater;
    wherein the portable device contains less than about 20 kJ reserved water energy where the liquid comprises an aqueous liquid; and
    wherein as compared to the liquid feed, the vapor produced by the device exhibits a reduction of at least 99.99% in a number of colony forming units as compared the number of colony forming units initially present in the liquid feed.

16. The vaporizer of claim 1, wherein passage of water containing a microbial count of 10$^6$ colony forming units through the portable device results in a reduction by at least 99.99% of the number of colony forming units.

17. The vaporizer of claim 16, further wherein during normal operation, an opportunity for scalding due to exposure to boiling liquid is essentially nonexistent.

18. A method for generating pressurized vapor from an unpressurized liquid, comprising:
    a. providing a liquid feed to a portable vaporizer device, the liquid characterized as having a first pressure; and
    b. vaporizing the liquid to produce a vapor, the vapor characterized as having a second pressure;

wherein the second pressure is greater than the first pressure;

wherein the portable vaporizer device comprises a porous member, a heater, and a mechanical force generator for providing compressive force among the porous member and the hearer; and wherein as compared to the liquid feed, the vapor produced by the portable vaporizer device exhibits a reduction of at least 99.99% in the number of colony forming units as compared the number of colony forming units initially present in the liquid feed.

19. The portable vaporizer of claim 1, wherein as compared to an unpressurized aqueous liquid feed, the vapor produced by the device exhibits a reduction of at least 99.99% in the number of colony forming units as compared the number of colony forming units initially present in the liquid feed.

20. The portable vaporizer of claim 19, further wherein during normal operation, an opportunity for scalding due to exposure to boiling liquid is essentially nonexistent.

* * * * *